(12) United States Patent  
Ross et al.

(10) Patent No.: US 6,726,720 B2
(45) Date of Patent: Apr. 27, 2004

(54) MODULAR DISC PROSTHESIS

(75) Inventors: Raymond Ross, West Didsburg (GB); Michael O'Neil, West Barnstable, MA (US); Mark Boomer, Somerville, MA (US)

(73) Assignee: DePuy Spine, Inc., Raynaham, MA (US)

( * ) Notice: Subject to any disclaimer, the term of this patent is extended or adjusted under 35 U.S.C. 154(b) by 0 days.

(21) Appl. No.: 10/108,196

(22) Filed: Mar. 27, 2002

(65) Prior Publication Data

US 2003/0187506 A1 Oct. 2, 2003

(51) Int. Cl.$^7$ ................................. A61F 2/44
(52) U.S. Cl. ................... 623/17.15; 623/17.13
(58) Field of Search ................ 623/17.11, 17.15, 623/17.16, 17.13, 23.41, 21.15, 22.24, 23.17

(56) References Cited

U.S. PATENT DOCUMENTS

| | | |
|---|---|---|
| 4,759,769 A | 7/1988 | Hedman et al. |
| 5,071,437 A | 12/1991 | Steffee |
| 5,245,098 A | 9/1993 | Summers et al. |
| 5,246,458 A | 9/1993 | Graham |
| 5,306,309 A | 4/1994 | Wagner et al. |
| 5,429,863 A | 7/1995 | McMillin |
| 5,458,643 A | 10/1995 | Oka et al. |
| 5,514,180 A | 5/1996 | Heggeness et al. |
| 5,534,030 A | 7/1996 | Navarro et al. |
| 5,571,109 A | 11/1996 | Bertagnoli |
| 5,674,294 A | 10/1997 | Bainville et al. |
| 5,683,465 A | 11/1997 | Shinn et al. |
| 5,741,253 A | 4/1998 | Michelson |
| 5,776,196 A | 7/1998 | Matsuzaki et al. |
| 5,824,094 A | 10/1998 | Serhan et al. |
| 5,865,846 A | 2/1999 | Bryan et al. |
| 5,893,889 A | 4/1999 | Harrington |
| 6,258,125 B1 | 7/2001 | Paul et al. |
| 6,261,586 B1 | 7/2001 | McKay |
| 6,270,528 B1 | 8/2001 | McKay |
| 2002/0029084 A1 * | 3/2002 | Paul et al. .............. 623/23.63 |
| 2002/0035400 A1 * | 3/2002 | Bryan et al. ............ 623/17.15 |

FOREIGN PATENT DOCUMENTS

| | | |
|---|---|---|
| US | 2001/0039456 | 11/2001 |
| US | 2001/0039457 | 11/2001 |
| US | 2001/0039458 | 11/2001 |
| US | 2001/0041941 | 11/2001 |
| US | 2001/0047208 | 11/2001 |
| US | 2001/0049560 | 12/2001 |
| US | 2001/0056302 | 12/2001 |
| US | 2002/0029084 | 3/2002 |
| WO | WO 01/49220 | 7/2001 |
| WO | WO 01/62191 | 8/2001 |
| WO | WO 01/66048 | 9/2001 |
| WO | WO 01/70137 | 9/2001 |
| WO | WO 01/78798 | 10/2001 |

OTHER PUBLICATIONS

*Surgical Technique Using FRA Spacer Instruments: Technique Guide*, Synthes Spine, pp. 1–16 (1998).
*Keystone Graft Instruments*, Pamphlet by DePuy Motech, Inc., 6 pages (1998).

* cited by examiner

*Primary Examiner*—Corrine McDermott
*Assistant Examiner*—Alvin Stewart
(74) *Attorney, Agent, or Firm*—Nutter McClennen & Fish LLP

(57) ABSTRACT

A modular implant that is effective to replace a damaged or degenerated spinal disc is provided. The implant includes a central core member having superior and inferior surfaces, a superior endplate member having a bone-contacting surface and a mating surface effective to mate with the superior surface of the central core member, and an inferior endplate member having a bone-contacting surface and a mating surface effective to mate with the inferior surface of the central core member. The modularity of the implant allows the surgeon to select and properly fit each modular endplate member separately during the surgical procedure, thereby eliminating the need to prepare the endplates of each adjacent vertebrae, and/or the bone-contacting surfaces of the implant.

29 Claims, 7 Drawing Sheets

MODULAR DISC PROSTHESIS

FIELD OF THE INVENTION

The present invention relates to disc prosthesis, and more particularly, to a modular disc prosthesis which is effective to accommodate a variety of vertebral body endplates.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

In general, the ability to achieve bone fusion appears to be related to certain factors, such as the quality and quantity of bone graft material present, the surface area available for the fusion to occur over, and the stability of the construct being fused. The fusion cage and/or bone graft should, for example, occupy a significant portion of the disc space to provide a large surface area over which fusion can occur, and should contour the vertebral endplates adjacent the disc space to provide stability and further promote fusion. The fusion cage and/or bone graft used for the purpose of interbody fusion, however, cannot always be shaped to precisely fit the complex contours of the vertebral endplates adjacent the disc space. Moreover, the process of preparing and shaping an implant to contour adjacent vertebral endplates can be very time consuming.

Rather than shaping the fusion cage to contour the disc space, procedures have been developed to remove at least a portion of the outermost layer of the vertebral endplates. These procedures, however, can also present the surgeon with several challenges. The vertebral endplates should be prepared to match the implant to provide the greatest possible interface congruity between the endplates and the implant, as well as provide for the optimal contact surface, enhanced fusion area, and enhanced graft and construct stability. In order to achieve this, the amount of bone removed must be to a specified depth and width. Excess removal or penetration of the vertebral endplate can result in a weakening of the structural integrity of the vertebrae, thereby potentially causing the vertebral bodies to collapse around the fusion implant. Moreover, if the shape of the vertebral endplates does not match the shape of the implant, shifting can occur resulting in misalignment of the vertebrae.

Accordingly, there is a need for an implant which allows greater modularity to accommodate a variety of vertebral body endplates, without requiring the vertebral endplates to be prepared or the implant to be shaped and prepared during the procedure.

SUMMARY OF THE INVENTION

The present invention provides a modular implant for promoting fusion of adjacent vertebrae to the implant, and optionally provides a shock-absorbing function. The modularity of the implant allows the surgeon to select components which have a shape and size that conforms to the complex contours of the vertebral endplates adjacent the disc space. In general, the implant includes a central core member having superior and inferior surfaces, a superior endplate member having a bone-contacting surface and a mating surface effective to mate with the superior surface of the central core member, and an inferior endplate member having a bone-contacting surface and a mating surface effective to mate with the inferior surface of the central core member. The superior and inferior endplate members can be adapted to fixedly engage the central core member.

The superior and inferior surfaces of the central core member can each include an attachment member adapted to mate with the superior and inferior endplate members, respectively. The attachment members can be mated to the central core member, and can be slidably matable with the endplate members. The modular implant can further include a connecting element disposed on the superior and inferior attachment members and effective to slidably mate the superior and inferior attachment members to the superior and inferior endplate members. In one aspect, the implant includes a posterior portion and an anterior portion, and the superior and inferior endplate members are slidably matable with the superior attachment members in the posterior and anterior directions or, alternatively, in a posterio-lateral or anterio-lateral direction.

In one embodiment, the connecting element is a first complementary member formed on each of the superior and inferior attachment members, and a second complementary member formed on each of the endplate members. The first complementary member, e.g., a female dovetail, is slidably matable with the second complementary member, e.g., a male dovetail. In another embodiment, the connecting element can be formed from at least one protruding element formed on one of the attachment members and the endplate members, and at least one bore formed on the other one of the attachment members and the endplate members. The protruding element is adapted to be disposed within the bore to mate each endplate member to the attachment members of the central core.

The modular implant can optionally include a locking mechanism formed on at least one of the attachment members and the endplate members. The locking mechanism is effective to fixedly engage the superior attachment member to the superior endplate member and the inferior attachment member to the inferior endplate member. In one embodiment, the locking mechanism is a bore which extends through the complementary male and female dovetail complements, and a pin slidably disposed through the bore. The pin is effective to prevent movement of the attachments members with respect to the endplate members. In another embodiment, the locking mechanism can be a bore which extends through the attachment member and the endplate member, and a pin member adapted to be disposed through the bore.

The modular implant system of the invention can include a plurality of superior and inferior endplate members. The bone-contacting surfaces of the various superior and inferior endplate members can each have specific geometries and sizes adapted to conform to vertebral body endplates of various shapes and sizes. The geometries of the superior and inferior endplate members can be, for example, a convex shape, a domed shape, a serpentine shape, a ramped shape, and an angled shape, and combinations thereof. This type of modular system allows surgeons to construct an implant having superior and inferior endplate members which are adapted to fit within the vertebral space.

The present invention also provides a method for inserting an implant between a superior vertebrae and an inferior vertebrae.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a modular implant that is effective to replace a damaged or degenerated spinal disc. In general, the implant includes modular endplate components having a variety of shapes and sizes. The modularity of the implant allows the surgeon to select and properly fit each modular endplate member separately during the surgical procedure, thereby minimizing endplate preparation of each adjacent vertebrae, and/or the bone-contacting surfaces of the implant.

Figure 1A:
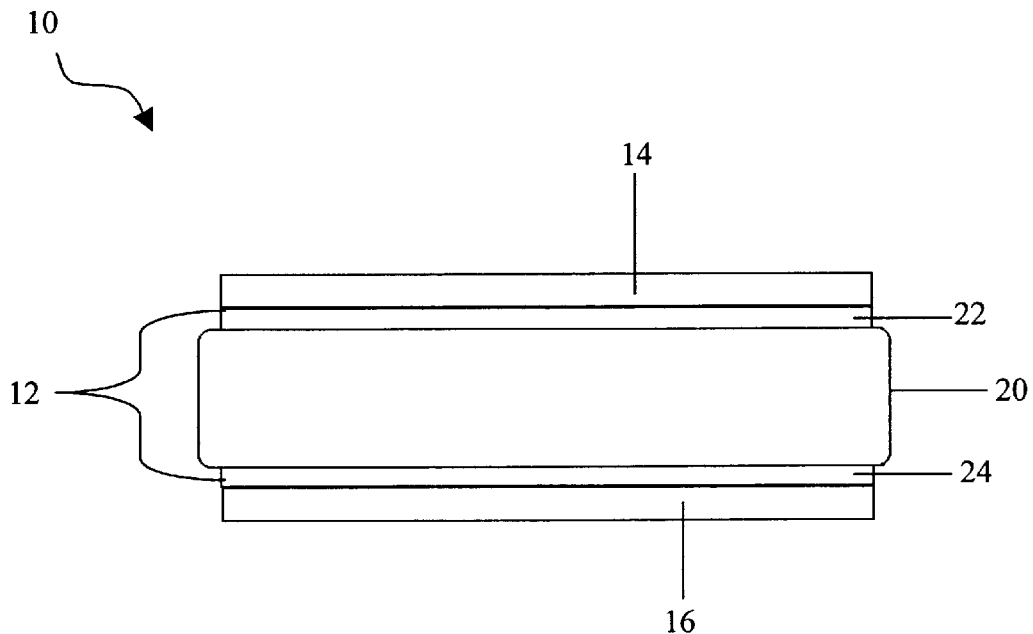
FIG. 1A is an side view illustration of a modular implant according to one embodiment of the present invention.
Figure 1B:
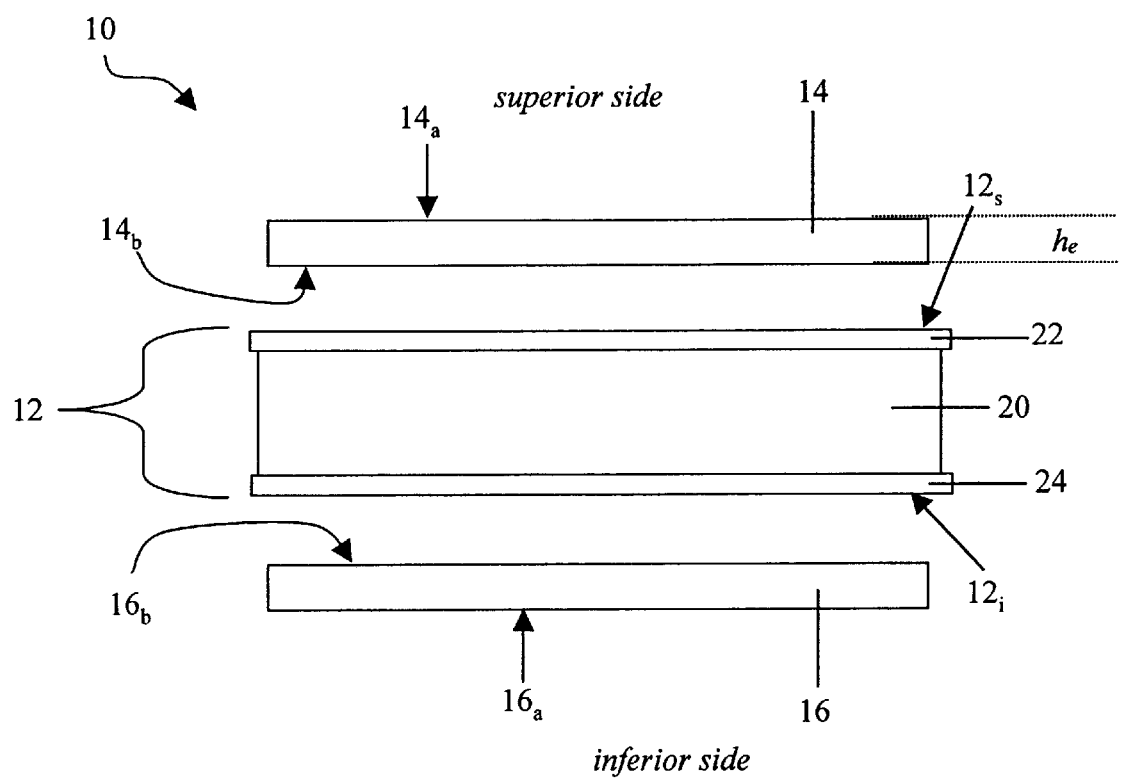
FIG. 1B is a side view illustration of the modular implant of FIG. 1A in the disassembled form.

As shown in FIGS. 1A and 1B, the implant 10 generally includes a central core member 12 having superior and inferior surfaces $12_s$, $12_i$, a superior endplate member 14 having a bone-contacting surface $14_a$ and a mating surface $14_b$ effective to mate with the superior surface $12_s$ of the central core member 12, and an inferior endplate member 16 having a bone-contacting surface $16_a$ and a mating surface $16_b$ effective to mate with the inferior surface $12_i$ of the central core member 12. The superior and inferior surfaces $12_s$, $12_i$ of the central core member 12 can include superior and inferior attachment members 22, 24 that are adapted to mate with the superior and inferior endplate members 14, 16, respectively.

Figure 2A:
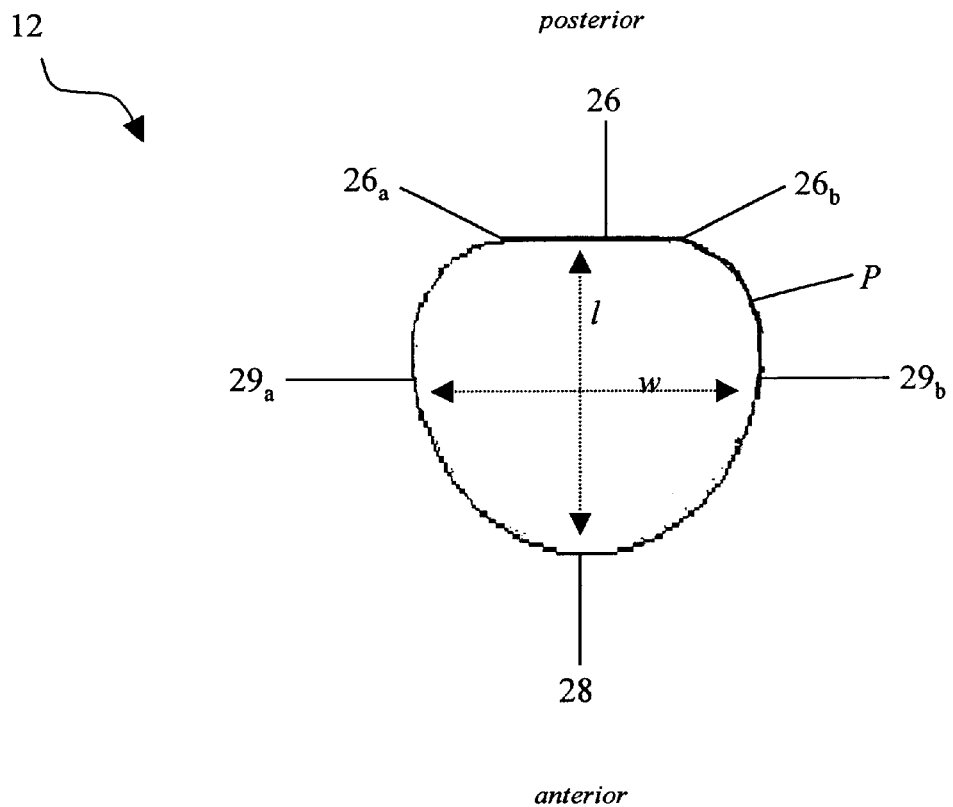
FIG. 2A is top view illustration of a central core member of the modular implant shown in FIG. 1A.
Figure 2B:
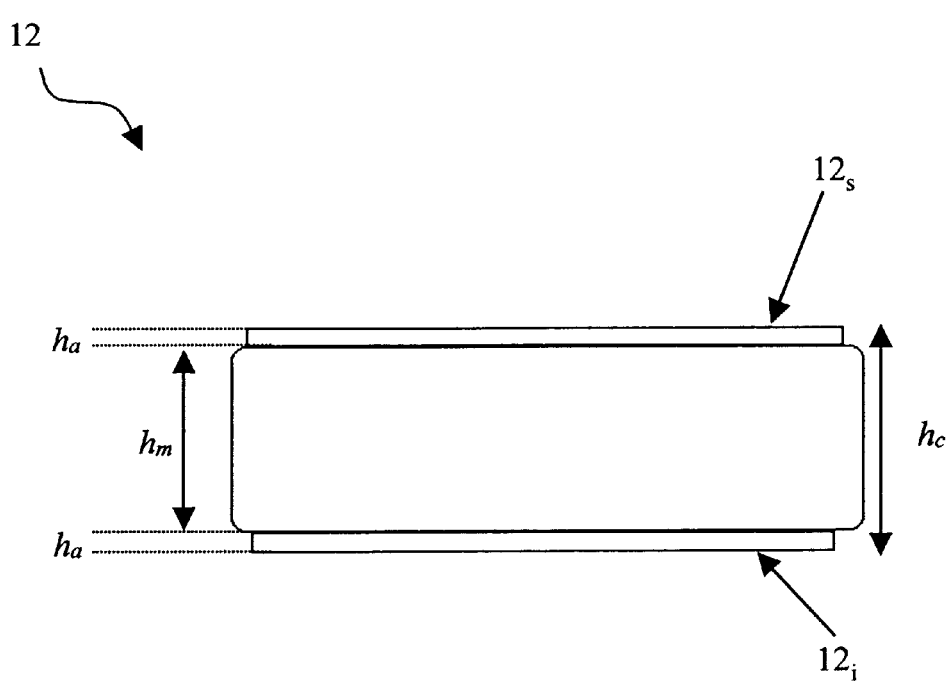
FIG. 2B is side view illustration of the central core member of FIG. 2A.

As shown in FIGS. 2A and 2B, the central core member 12 includes superior and inferior surfaces $12_s$, $12_i$, a posterior portion 26, an anterior portion 28, first and second lateral sides $29_a$, $29_b$, and a perimeter P. The central core member 12 can have virtually any shape, but is preferably designed to generally conform to the shape of a natural human spinal disc, as shown in FIG. 2A. The posterior portion 26 of the central core member 12 is substantially flat, while the anterior portion 28 and the lateral sides $29_a$, $29_b$ form a curved convex portion of the perimeter between opposite ends $26_a$, $26_b$ of the flattened posterior portion 26. Referring to FIG. 2B, the central core member 12 has a height $h_c$, which can vary depending on the height of each endplate member 14, 16, as well as the amount of space available between the adjacent vertebral bodies where the implant 10 is to be inserted. Preferably, the height $h_c$ of the central core member 12, when combined with the height of each endplate member, is sufficient to fit within the vertebral space. Preferably, the height $h_c$ is generally in the range of about 5 mm to 15 mm.

As shown in FIGS. 1A, 1B and 2B, the central core member 12 can include superior and inferior attachment members 22, 24 which form the superior and inferior surfaces $12_s$, $12_i$ of the central core member 12. The attachment members 22, 24 can be rigid plate-like members which are removably or fixedly attached to a core component 20, and together the attachment members 22, 24 and the core component 20 form the central core member 12.

The core component 20 can be formed from a variety of materials, and can be rigid, semi-rigid, or flexible. Preferably, the core component 20 is formed from a compliant material that is adapted to provide a shock-absorbing function when implanted between adjacent vertebrae. Suitable materials from which the core component 20 can be made include an elastomeric material, a polyolefin rubber or carbon black reinforced polyolefin rubber. In use, the core component 20 is effective to simulate the characteristics of a natural disc. Although the elastomeric core is disclosed as being made of a polyolefin rubber, it can be made of any elastomeric material that simulates the characteristics of a natural disc. Alternatively, the core component 20 can be made of a rigid material, such as a biocompatible metal.

The core component 20 and each attachment member 22, 24 has a height $h_m$, $h_a$, respectively (FIG. 2B). The combined heights of the core component 20 and the attachment members 22, 24 equals the total height $h_c$ of the central core member 12. The height $h_a$ of the superior attachment member 22 can be different than the height $h_a$ of the inferior attachment member 24, but preferably the height $h_a$ of each attachment member 22, 24 is substantially less than the height $h_m$ of the core component 20. In a preferred embodiment, the height $h_a$ of each attachment member 22, 24 is generally in the range of about 1 mm to 3 mm, and the height $h_m$ of the core component 20 is generally in the range of about 2 mm to 10 mm.

Referring back to FIG. 2A, while the dimensions of the central core member 12 can vary, the central core member 12 preferably has a length l in the anterior-posterior direction in the range of about 20 mm to 40 mm, and a width w in the medial-lateral direction in the range of about 25 mm to 50 mm. The superior and inferior attachment members 22, 24 are preferably identical to each other, and have a perimeter similar or identical to the perimeter of the core component 20. However, the attachment members 22, 24 can have a perimeter slightly smaller than or slightly larger than the perimeter of the core component 20.

The attachment members 22, 24 can be fixedly attached to or removably mated to the core component 20 using a variety of attachment mechanisms. For example, the attachment members 22, 24 can be ultrasonically welded, adhesively secured, or mechanically connected to the core component 20. In an exemplary embodiment, each attachment member 22, 24 is compression molded to the core component 20. U.S. Pat. No. 5,824,094 entitled "Spinal Disc," by Serhan et al., which is expressly incorporated by reference herein, discloses an exemplary central core member 12.

Referring back to FIG. 1B, the implant 10 includes superior and inferior endplate members 14, 16, and each endplate member 14, 16 has a bone-contacting surface $14_a$, $16_a$ and a mating surface $14_b$, $16_b$ that is joined to the central core member 12. The superior endplate member 14 is preferably the mirror image of the inferior endplate member 16, and each endplate member 14, 16 has a perimeter substantially the same as the perimeter P (FIG. 2A) of the central core member 12. The perimeter of each endplate member 14, 16 can vary however, and can be slightly less than or slight larger than the perimeter P of the central core member 12. A person having ordinary skill in the art will appreciate that the superior and inferior endplate members 14, 16 can have a variety of shapes, sizes, and/or features present on one of both of the endplate members 14, 16.

As shown in FIG. 1B, each endplate member 14, 16 has a height $h_e$ which can vary depending on the height $h_c$ of the central core member 12, as well as the amount of space available between the adjacent vertebral bodies where the implant 10 is to be inserted. Preferably, the height $h_e$ is generally in the range of about 1 mm to 5 mm. The length and width of the endplate members 14, 16 are preferably about the same as the length l and width w of the central core member 12, as shown in FIG. 2A.

Figure 3A:
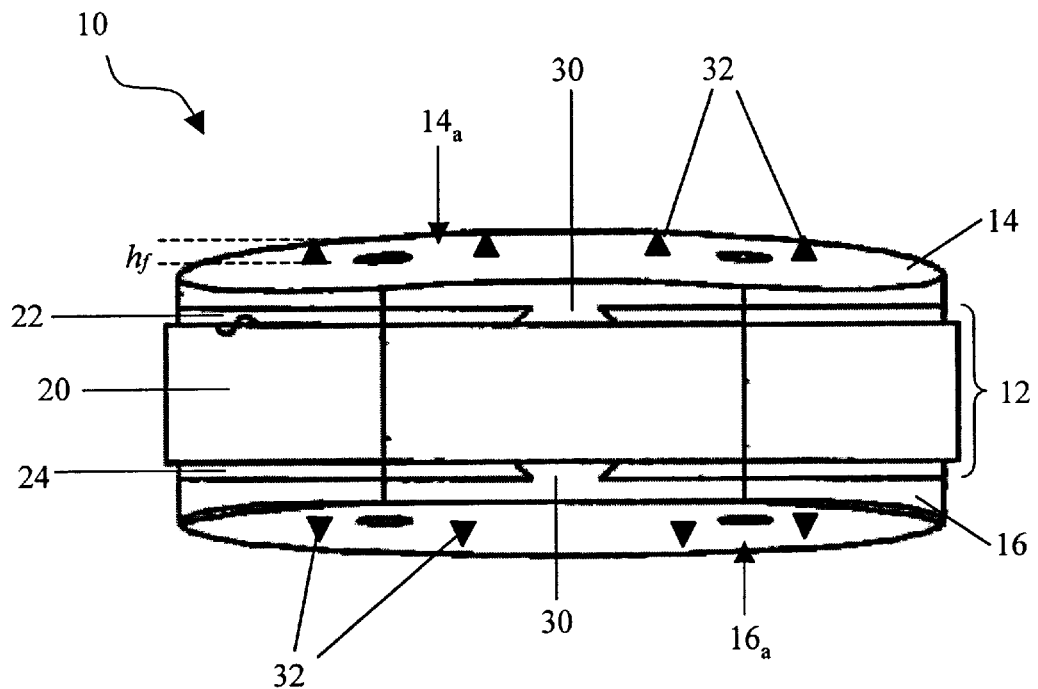
FIG. 3A is a side view illustration of one embodiment of a modular implant having a connecting element and bone-engaging surface features.
Figure 3B:
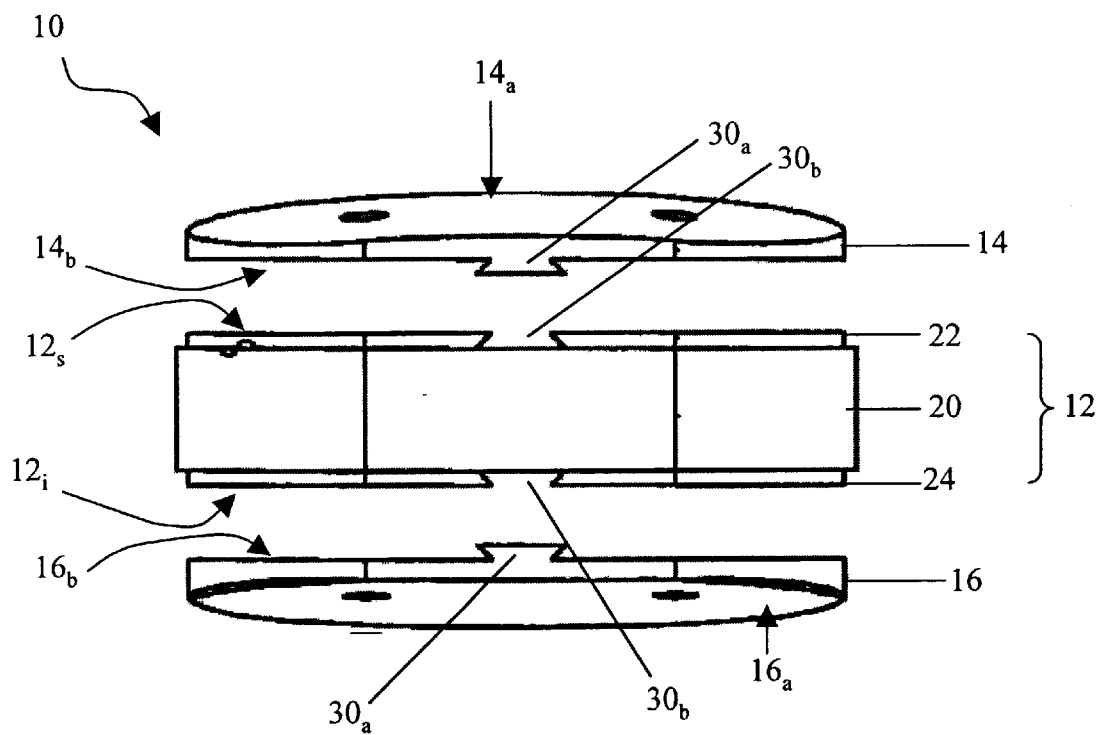
FIG. 3B is a side view illustration of the modular implant of FIG. 3A in the disassembled form.

While the bone-contacting surfaces $14_a$, $16_a$ of the endplate members 14, 16 can be parallel to one another, as shown in FIG. 1B, one or both of the endplate members 14, 16 preferably has a bone-contacting surface $14_a$, $16_a$ adapted to match the endplate of a human vertebrae. Thus, the shape and contour of the bone-contacting surfaces $14_a$, $16_a$ can vary. By way of non-limiting example, one or both of the bone-contacting surfaces $14_a$, $16_a$ of the endplate members 14, 16 can have a wedge-like shape (not shown) wherein one side (e.g., posterior) of the endplate member has a height less than the height of the opposed side (e.g., anterior) of the endplate member 14, 16. Other profiles include, for example, a supine shape, a converging portion, a domed or convex-like profile (FIGS. 3A and 3B). One of ordinary skill in the art will appreciate that various combinations of these profiles may be used as well.

In an exemplary embodiment, several superior and inferior endplate members 14, 16 are provided, each having a bone-contacting surface $14_a$, $16_a$ with a different size or shape. Thus, a superior endplate member 14 can be selected to match the shape of the superior endplate of the vertebral body where the implant is to be positioned, and an inferior endplate member 16 can be selected to be complimentary to the shape of the inferior endplate of the vertebral body where the implant is to be positioned. This affords a surgeon greater versatility to select superior and inferior endplate members 14, 16 to form an implant 10 with an optimal fit within the vertebral space. The endplate members 14, 16 can also vary in height to allow the surgeon to construct an implant having the necessary height to fit within the vertebral space. A person having ordinary skill in the art will appreciate that the endplate members 14, 16 can have virtually any shape and size.

As shown in FIG. 3A, the bone-contacting surfaces $14_a$, $16_a$ can optionally include a plurality of bone-engaging surface features, or fins 32, to enhance secure implantation of the implant 10 at the desired location, and to prevent the expulsion of the implant from its implantation location. The fins 32 can vary in shape, number, and in their placement on either or both of the bone-contacting surfaces $14_a$, $16_a$ of the endplate members 14, 16. Selected regions of the bone-contacting surfaces $14_a$, $16_a$ can be free of surfaces features. The fins 32 preferably extend from and are integral with the bone-contacting surfaces $14_a$, $16_a$ of the endplate members 14, 16. The fins 32 may take on a variety of shapes and sizes, but preferably are in the form of discrete, pyramid-shaped teeth. Each fin 32 should have a size sufficient to enable it to engage and penetrate any bone adjacent to which it is positioned. In an exemplary embodiment, each fin 32 has a height $h_f$ generally in the range of about 0.5 to 7 mm.

The endplate members 14, 16 and the attachment members 22, 24 can be made of any suitable biocompatible material, including but not limited to a composite plastic material. Each endplate member 14, 16 and attachment member 22, 24 is preferably milled out of a single block of metal, but could be made by casting. Preferably, the endplate members 14, 16 and the attachment members 22, 24 are made of a biocompatible rigid metal such as a titanium-vanadium-aluminum alloy having about 90% by weight titanium, about 6% by weight aluminum, and about 4% by weight vanadium.

The endplate members 14, 16 can be placed adjacent each attachment member 22, 24 and sandwiched together within the vertebral space. Alternatively, a connecting element can be provided for mating, and optionally locking, the endplate members 14, 16 to the respective attachment members 22, 24. A person having ordinary skill in the art will appreciate that virtually any type of connecting element can be used to removably or fixedly attach the endplate members 14, 16 to the central core member 12. By way of non-limiting example, the endplate members 14, 16 can be mated the central core member 12 using a positive interlock engagement, an interference fit, a threaded engagement, an adhesive, or any other type of engagement element.

FIGS. 3A–6 illustrate exemplary embodiments of a connecting element effective to mate the endplate members 14, 16 to the attachment members 22, 24. The connecting element can also serve as a positive locking element to prevent virtually any movement of the components with respect to each other. The implant 10 can include a single connecting element, or the implant 10 can include a combination of connecting elements.

FIGS. 3A–4B illustrate one embodiment of a connecting element 30 which is effective to allow each endplate member to slidably mate to the corresponding attachment member 22, 24. The connecting element 30 can be formed on one or both of the attachment members 22, 24 and the mating surface $14_b$, $16_b$ of each endplate member 14, 16. In one embodiment, the connecting element 30 is a dovetail connection having complementary components $30_a$, $30_b$. As shown in FIG. 3B, the mating surface $14_b$ of the superior endplate member 14 includes a female dovetail $30_a$, and the superior surface $12_s$ of the superior attachment plate 22 of the central core member 12 includes a complementary, male dovetail $30_b$. The male and female dovetail components $30_a$, $30_b$ are adapted to slidably mate to one another. While FIGS. 3A and 3B illustrate the endplate members 14, 16 having a male dovetail 30b, and the attachment members 22, 24 having a female dovetail $30_a$, the location of the male and female dovetails $30_a$, 30b can be reversed. The complementary members can be dimensioned to provide a frictional or interference fit to fixedly or securely mate the endplate members 14, 16 to the attachment members 22, 24 when the endplate members 14, 16 and attachment members 22, 24 are properly positioned with respect to each other. One of ordinary skill in the art will appreciate that a dovetail connecting element is described only for exemplary purposes; a variety of other complementary connecting members can alternatively be used.

Figure 4A:
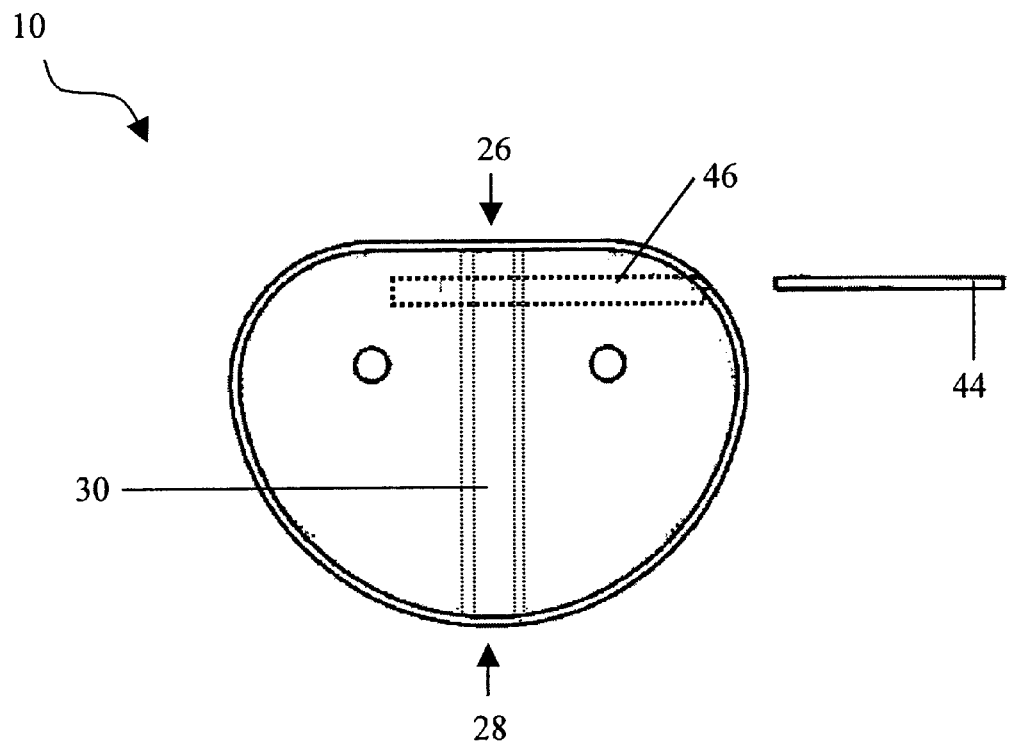
FIG. 4A is a top view illustration of a modular implant having a connecting element and a locking element.
Figure 4B:
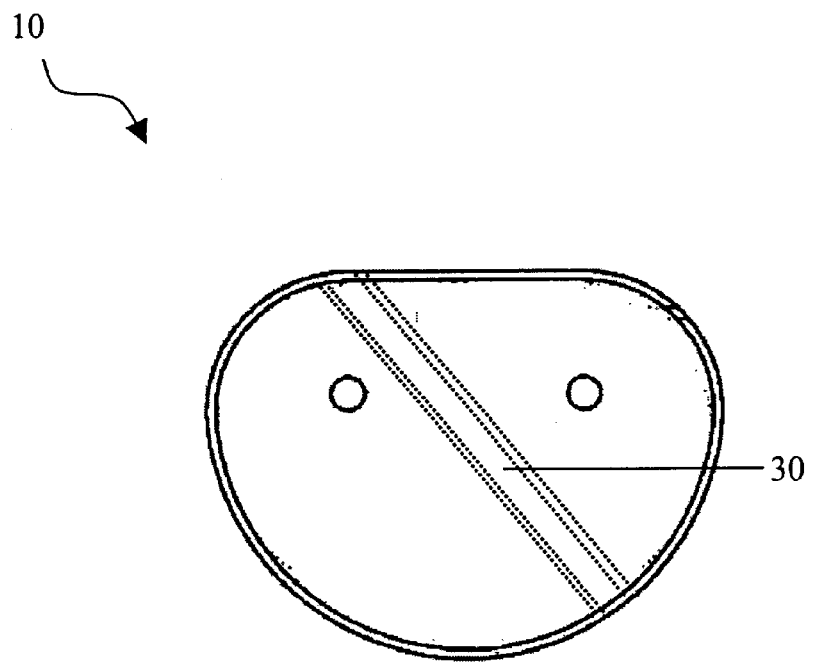
FIG. 4B is a top view illustration of another embodiment of a modular implant having a connecting element extending in an anterio-lateral or posterio-lateral direction.

As shown in FIG. 4A, the connecting element 30 can extend between the posterior side 26 and the anterior side 28 of the implant 10, such that the endplate members 14, 16 are slidably matable to the attachment members 22, 24 in a posterior-anterior direction. Alternatively, where an anterio-lateral or posterio-lateral surgical approach is used to insert the implant 10 between adjacent vertebral bodies, the connecting element 30 can extend in an anterio-lateral or posterio-lateral direction, as shown in FIG. 4B.

FIG. 4A illustrates another embodiment of a connecting element in which the implant includes a positive locking mechanism which is effective to prevent virtually any movement of the endplate members 14, 16 with respect to the central core member 12. The locking mechanism relies on the engagement of a pin 44 within a bore 46 which extends through both complementary dovetail components 30a, $30_b$. When the pin 44 is inserted into the bore 46, movement of the endplate members 14, 16 with respect to the attachment members 22, 24 is prevented.

Figure 5:
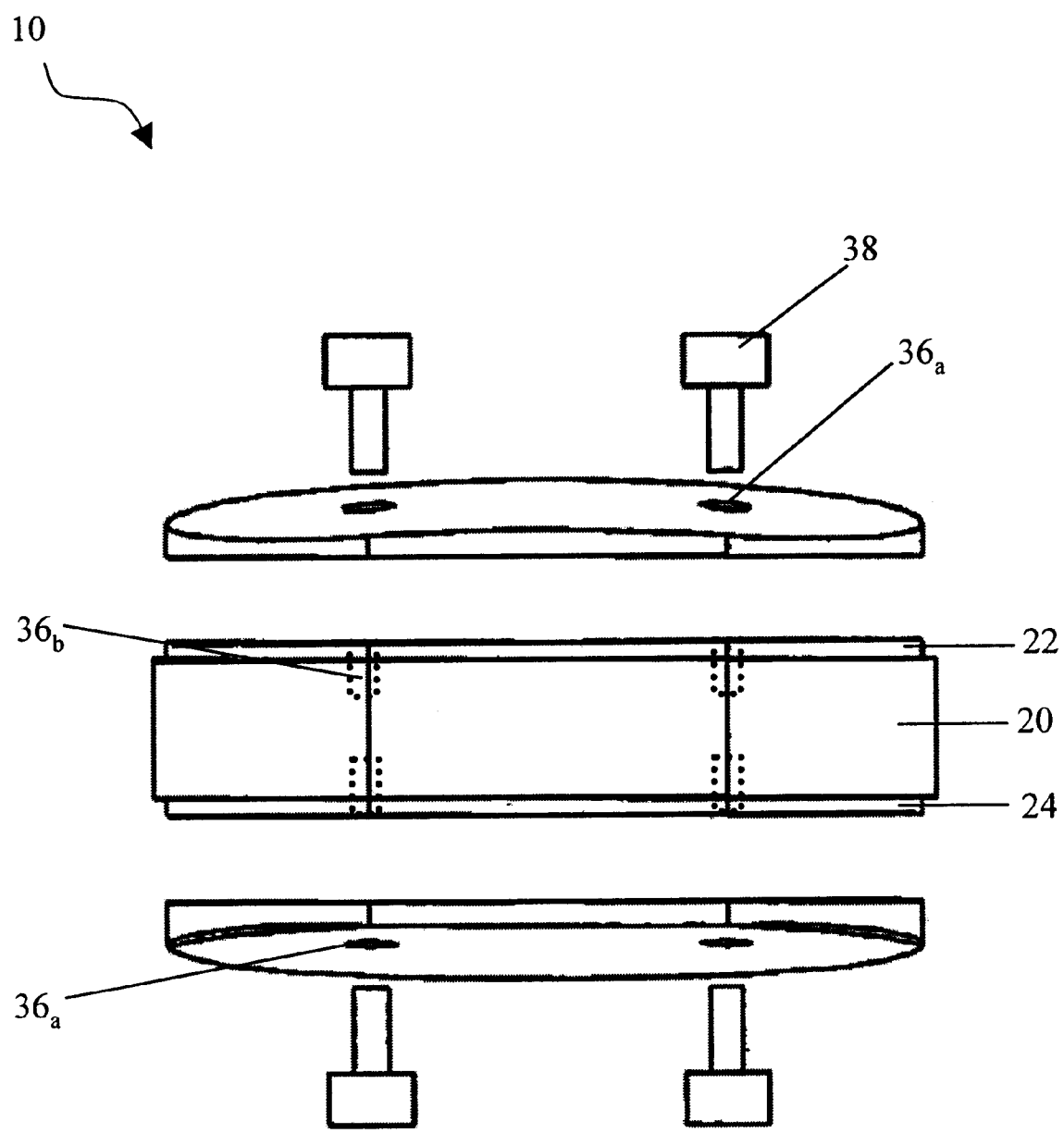
FIG. 5 is a side view illustration of a disassembled modular implant having a connecting element according to yet another embodiment of the present invention.

In an embodiment shown in FIG. 5, the endplate members 14, 16 and the attachment members 22, 24 include several bores 36 formed therein. The bores 36 can be blind bores that extend into the central core member 12 from the superior and/or inferior surfaces thereof. The bores 36 can also extend into the attachments members 22, 24, or they can extend through the attachment members 22, 24 and into the core component 20. Each bore 36 is adapted to receive a corresponding pin 38 to effect a locking engagement between the endplate members 14, 16 and the central core member 12. The bores $36_a$ in the endplate members 14, 16 should align with the bores $36_b$ in the attachment members 22, 24 to allow the each pin 38 to be inserted through both bores $36_a$, $36_b$ to secure the endplate members 14, 16 to the attachment members 22, 24. In one embodiment, the bores 36 can be threaded to receive a corresponding threaded pin 38. Alternatively, the pin 38 and/or the bores 36 can be tapered (not shown) to provide a frictional locking engagement between each pin 38 and each bore 36, or one of the pin 38 or bore 36 can include a detent (not shown), and the corresponding pin 38 or bore 36 can include a corresponding ridge adapted to fit within the detent to provide a positive locking engagement. The bores $36_b$ in the attachment members 22, 24 can extend through a portion of the attachment members 22, 24, entirely through the attachment members 22, 24, or through both the attachment members 22, 24 and into the core component 20. In an embodiment in which the bores 36 extend through the attachment members 22, 24 and into the core component 20, the pin 38 can be used to secure the attachment members 22, 24 to the core component 20.

Figure 6:
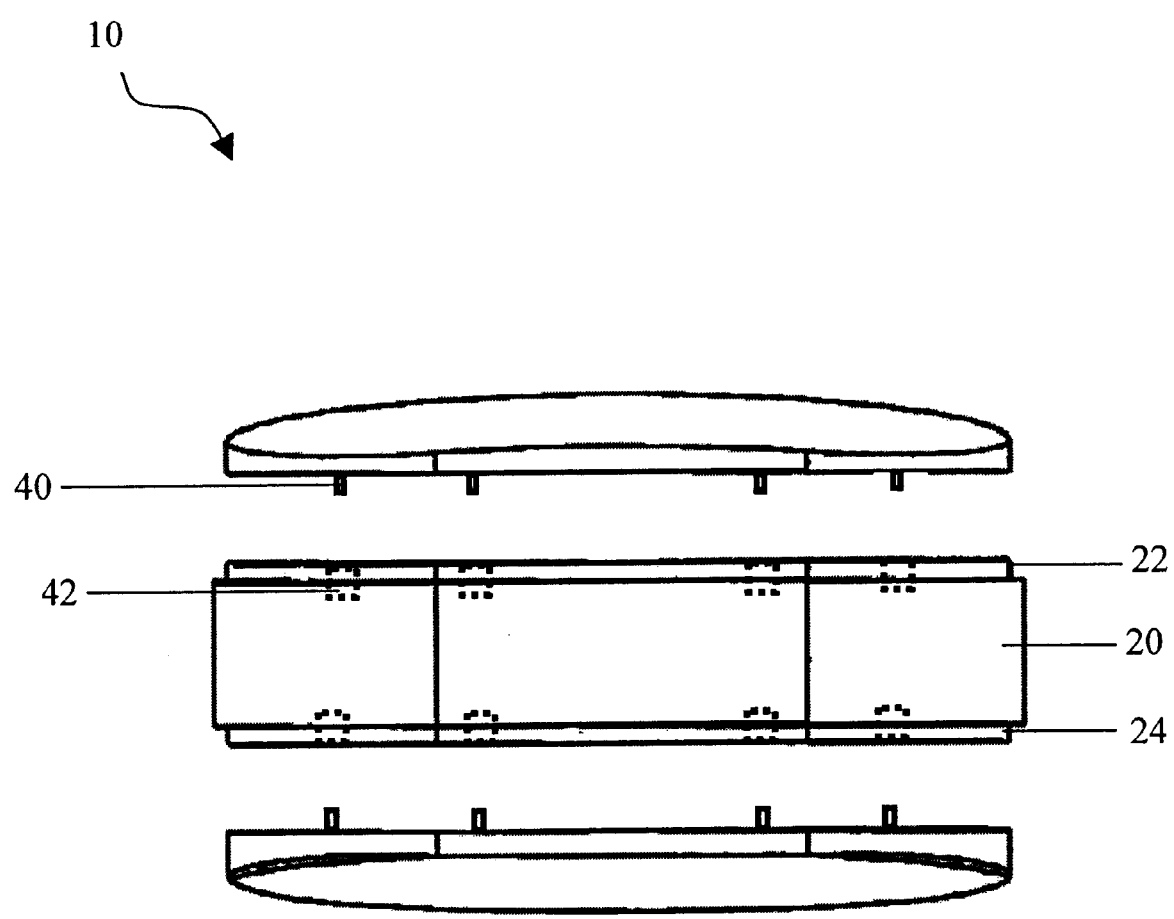
FIG. 6 is a side view illustration of another embodiment of a modular implant having a connecting element.

FIG. 6 illustrates another embodiment of a connecting element. As shown, the endplate members 14, 16 each include several protruding elements 40 that are complementary with apertures 42 formed in the attachment members 22, 24. The protruding elements 40 are adapted to be mated to the apertures 42 when each endplate member 14, 16 is mated to the central core member 12. The engagement of the protruding elements 40 and apertures 42 prevent slidable movement of the endplate members 14, 16 with respect to the central core member 12. The apertures 42 and/or the protruding elements 40 can also be adapted to provide a positive locking engagement between the endplate members 14, 16 and the central core member 12. For example, the apertures 42 and/or the protruding elements 40 can be tapered to provide a frictional engagement between each protruding element 40 and each aperture 42. Alternatively, the apertures 42 can include a detent (not shown), and each protruding member 40 can include a corresponding ridge (not shown) adapted to fit within and lock with the detent.

Figure 7:
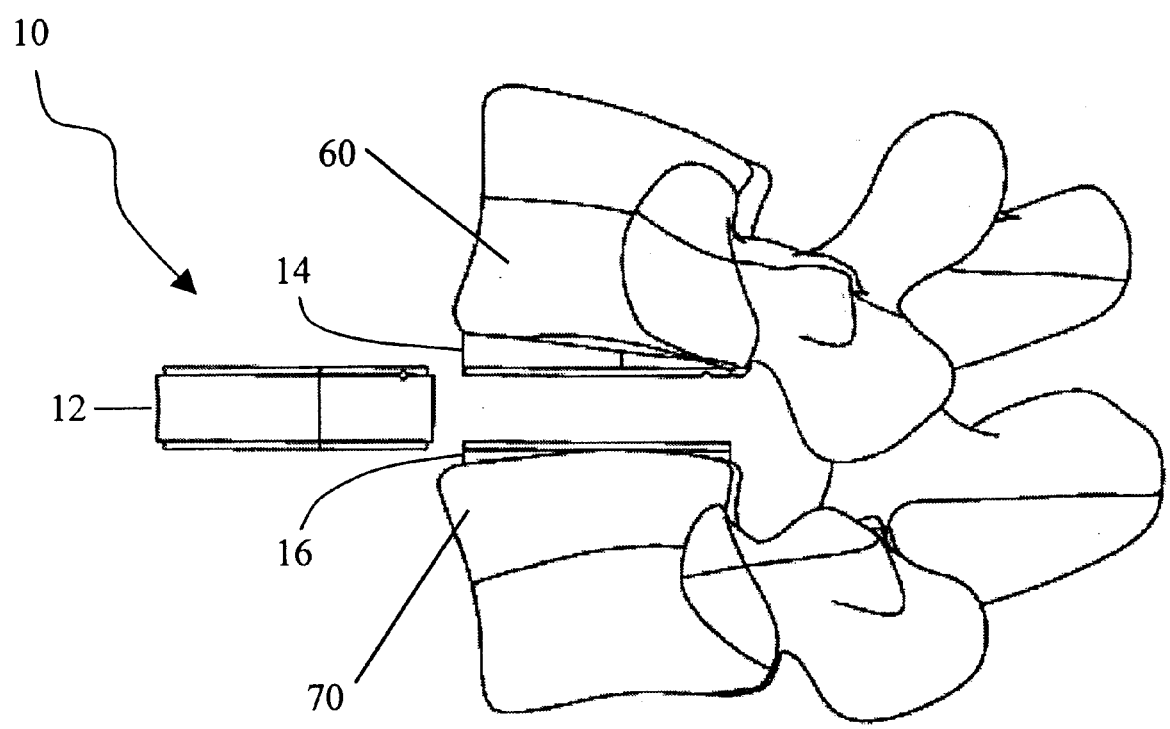
FIG. 7 is a side view illustration of a modular implant having superior and inferior endplate members positioned between adjacent vertebrae and having a central core member adapted to slidably mate to the superior and inferior endplate members.

In use, the endplate members 14, 16 are selected to construct an implant 10 that will best fit the anatomy of a given patient. Depending on the type of connecting element provided, the implant 10 can be constructed prior to insertion between adjacent vertebrae (intraoperative assembly). Alternatively, as shown in FIG. 7, the endplate members 14, 16 can first be positioned and installed upon the superior and inferior endplates of the vertebral bodies 60, 70 (in-situ assembly). Thereafter, the central core member 12 can then be inserted between and connected to the endplate members 14, 16 to construct the implant within the vertebral space.

A variety of medical tools can be used to separate the adjacent vertebrae, position the endplate members 14, 16 and insert the central core member 12, or to insert the pre-constructed implant into the vertebral space. Thus, the implant 10 can include features which are effective to permit the implant 10 to be used in connection with an insertion tool. By way of non-limiting example, the superior and inferior surfaces $12_s$, $12_i$ of the central core member 12 can each include a groove which is adapted to receive a lever of an inserter tool.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular implant, comprising:
    a central core member having superior and inferior surfaces with superior and inferior attachments members;
    a superior endplate member having a bone-contacting surface and a mating surface with a first complementary connecting element slidably matable with a second complementary connecting element on the superior attachment member on the superior surface of the central core member;
    an inferior endplate member having a bone-contacting surface and a mating surface with a first complementary connecting element slidably matable with a second complementary connecting element on the inferior attachment member on the inferior surface of the central core member.

2. The modular implant of claim 1, wherein the attachment members are adhesively mated to the central core member.

3. The modular implant of claim 1, wherein the complementary connecting elements comprise a female dovetail formed on one of the attachment members and the endplate members, and a complementary male dovetail formed on the other one of the attachment members and the endplate members.

4. The modular implant of claim 3, further comprising a bore extending through the complementary male and female dovetail components, and a pin slidably disposed through the bore, the pin being effective to prevent movement of the attachment members with respect to the endplate members.

5. The modular implant of claim 1, wherein the complementary connecting elements comprise at least one protruding element formed on one of the attachment members and the endplate members, and at least one bore formed on the other one of the attachment members and the endplate members, the bore being adapted to receive the protruding element.

6. The modular implant of claim 1, wherein the bone-contacting surfaces of the superior and inferior endplate members each have a shape adapted to conform to the endplates of adjacent vertebral bodies.

7. The modular implant of claim 6, wherein the shape of the bone-contacting surfaces of the superior and inferior endplate members is selected from the group consisting of a convex shape, a domed shape, a serpentine shape, a ramped shape, and an angled shape, and combinations thereof.

8. The modular implant of claim 1, further comprising a locking mechanism formed on at least one of the attachment members and the endplate members, the locking mechanism being effective to fixedly engage the superior attachment member to the superior endplate member and the inferior attachment member to the inferior endplate member.

9. The modular implant of claim 8, wherein the locking mechanism comprises a bore extending through the attachment member and the endplate member, and a pin member adapted to be disposed through the bore.

10. The modular implant of claim 1, wherein the implant includes a posterior portion and an anterior portion, and the superior and inferior endplate members are slidably matable with the superior and inferior attachment members in the posterior and anterior directions.

11. The modular implant of claim 1, wherein the implant includes a posterior portion and an anterior portion, and the superior and inferior endplate members are slidably matable with the superior and inferior attachment members in a posterio-lateral direction.

12. The modular implant of claim 1, wherein the implant includes a posterior portion and an anterior portion, and the superior and inferior endplate members are slidably matable with the superior and inferior attachment members in an anterio-lateral direction.

13. The modular implant of claim 1, wherein the central core member is made from a polymeric material.

14. A modular implant, comprising:
a disc member having
a central core member having superior and inferior surfaces;
a superior attachment plate disposed on the superior surface of the central core member; and
an inferior attachment plate disposed on the inferior surface of the central core member;
a superior endplate member having a bone-contacting surface and an engagement surface effective to slidably mate with the superior attachment plate of the disc member; and
a first locking mechanism disposed between the superior endplate member and the superior attachment plate and effective to lock the endplate member to the disc member when the superior endplate member is mated to the superior attachment plate;
an inferior endplate member having a bone-contacting surface and an engagement surface effective to slidably mate with the inferior attachment plate of the disc member;
a second locking mechanism disposed between the inferior endplate member and the inferior attachment plate and effective to lock the endplate member to the disc member when the inferior endplate member is mated to the inferior attachment plate.

15. The modular implant of claim 14, wherein the disc member includes a posterior portion and an anterior portion, and the superior and inferior endplate members are slidably matable with the superior and inferior attachment plates in the posterior and anterior directions.

16. The modular implant of claim 14, wherein the locking mechanism comprises a complementary male and female dovetail members adapted to provide frictional engagement of the endplate members to the disc member.

17. The modular implant of claim 14, wherein at least a portion of the bone-contacting surface of at least one of the endplate members include a plurality of bone-engaging surface features.

18. The modular implant of claim 9, wherein the bone-contacting surfaces of the superior and inferior endplate members each have a shape selected from the group consisting of a convex shape, a domed shape, a serpentine shape, a ramped shape, and an angled shape, and combinations thereof.

19. The modular implant of claim 14, wherein the disc member is made from a polymeric material.

20. A modular implant system, comprising:
a central core member having a superior engagement plate fixedly disposed on a superior surface of the central core member, and an inferior engagement plate fixedly disposed on an inferior engagement surface;
a plurality of superior endplate members removably matable with the superior engagement plate on the superior surface of the central core member; and
a plurality of inferior endplate members removably matable with the inferior engagement plate on the inferior surface of the central core member;
wherein the superior and inferior engagement plates each include one of a female and male dovetail, and the plurality of superior and inferior endplate members each include the other of a female and male dovetail.

21. The modular implant system of claim 20, wherein the superior and inferior endplate members are slidably matable with the central core member.

22. The modular implant system of claim 21, wherein the central core member includes a posterior side, an anterior side, and first and second lateral sides, the male and female dovetails of the engagement plates and the endplate members extending in an anterio-lateral direction.

23. The modular implant system of claim 21, wherein the central core member includes a posterior side, an anterior side, and first and second lateral sides, the male and female dovetails of the engagement plates and the endplate members extending in a posterio-lateral direction.

24. The modular implant system of claim 20, wherein the superior and inferior endplate members each have an engagement surface matable with the superior and inferior engagement plates and a bone contacting surface, each bone contacting sruface of each endplate member having a shape adapted to mate with a vertebral endplate.

25. The modular implant system of claim 24, wherein the shape of the bone contacting surface of each endplate member is selected from the group consisting of a convex shape, a concave shape, a domed shape, an angled shape, and a serpentine shape.

26. The modular implant system of claim 20, wherein the central core member is made from a polymeric material and is compression molded to mate to the superior and inferior engagement plates.

27. The modular implant system of claim 20, wherein the male and female dovetails are adapted to provide a locking frictional engagement between the engagement plates and the endplates.

28. The modular implant system of claim 20, wherein the central core member includes a posterior side, an anterior side, and first and second lateral sides, the male and female dovetails of the engagement plates and the endplate members extending in an posterior-anterior direction.

29. A modular implant, comprising:

a central core member having a superior attachment plate disposed on a superior surface of the central core member, and an inferior attachment plate disposed on an inferior surface of the central core member, the central core member being made from a polymeric material and being compression molded to the superior and inferior attachment plates;

a superior endplate member having a bone-contacting surface and an engagement surface effective to mate with the superior attachment plate of the disc member; and an inferior endplate member having a bone-contacting surface and an engagement surface effective to mate with the inferior attachment plate of the disc member.

* * * * *